(12) United States Patent
Sutherland et al.

(10) Patent No.: US 12,239,781 B2
(45) Date of Patent: Mar. 4, 2025

(54) RELEASABLE MONITOR WITH OPTICAL DOSE COUNTER FOR A MEDICAMENT INHALER

(71) Applicant: Adherium (NZ) Limited, Auckland (NZ)

(72) Inventors: Garth Campbell Sutherland, Auckland (NZ); Michael James Gormack, Auckland (NZ); Pavel Bezmaternykh, Auckland (NZ)

(73) Assignee: Adherium (NZ) Limited, Auckland (NZ)

( * ) Notice: Subject to any disclaimer, the term of this patent is extended or adjusted under 35 U.S.C. 154(b) by 365 days.

(21) Appl. No.: 16/854,863

(22) Filed: Apr. 21, 2020

(65) Prior Publication Data

US 2020/0316321 A1    Oct. 8, 2020

Related U.S. Application Data

(63) Continuation-in-part of application No. 15/247,776, filed on Aug. 25, 2016, now Pat. No. 10,668,232, (Continued)

(30) Foreign Application Priority Data

Feb. 5, 2009   (NZ) ........................................ 574666

(51) Int. Cl.
*A61M 15/00*   (2006.01)
*G16H 20/10*   (2018.01)

(52) U.S. Cl.
CPC ...... *A61M 15/008* (2014.02); *A61M 15/0065* (2013.01); *A61M 15/0068* (2014.02);
(Continued)

(58) Field of Classification Search
CPC .......... A61M 15/0065; A61M 15/0068; A61M 15/008; G16H 20/10
See application file for complete search history.

(56) References Cited

U.S. PATENT DOCUMENTS

| | | | | |
|---|---|---|---|---|
| 5,590,645 A | * | 1/1997 | Davies | A61M 15/0045 |
| | | | | 128/203.15 |
| 5,921,237 A | * | 7/1999 | Eisele | A61M 15/0048 |
| | | | | 128/203.15 |
| 6,651,651 B1 | | 11/2003 | Bonney et al. | |
| 7,249,687 B2 | * | 7/2007 | Anderson | A61M 15/0043 |
| | | | | 221/3 |
| 2002/0189615 A1 | * | 12/2002 | Henry | A61M 15/0081 |
| | | | | 128/203.21 |

(Continued)

FOREIGN PATENT DOCUMENTS

WO    WO2007137991 A1    12/2007

*Primary Examiner* — Kathryn E Ditmer
(74) *Attorney, Agent, or Firm* — Kenealy Vaidya LLP

(57) ABSTRACT

Some embodiments are directed to a device for monitoring patient usage of a medicament inhaler, being adapted to deliver doses of medicament. The device includes a housing, for releasable attachment to the medicament inhaler, and a sensor configured to determine when a dose of medicament has been dispensed from the medicament inhaler. The device is attachable to the medicament inhaler, and is subsequently operable without any modifications being required to be made to the medicament inhaler. The device may also include an electronic control module which is in communication with the sensor, the electronic control module being adapted to monitor and/or store data relating to patient usage of the medicament inhaler.

10 Claims, 6 Drawing Sheets

Related U.S. Application Data which is a continuation of application No. 13/705,813, filed on Dec. 5, 2012, now Pat. No. 9,468,729, which is a continuation of application No. 12/381,145, filed on Mar. 6, 2009, now abandoned.

(52) U.S. Cl.
CPC .......... *A61M 15/009* (2013.01); *G16H 20/10* (2018.01); *A61M 15/0083* (2014.02); *A61M 2202/064* (2013.01); *A61M 2205/18* (2013.01); *A61M 2205/3313* (2013.01); *A61M 2205/3375* (2013.01); *A61M 2205/3553* (2013.01); *A61M 2205/3584* (2013.01); *A61M 2205/3592* (2013.01); *A61M 2205/502* (2013.01); *A61M 2205/52* (2013.01); *A61M 2205/581* (2013.01); *A61M 2205/583* (2013.01)

(56) References Cited

U.S. PATENT DOCUMENTS

| | | | |
|---|---|---|---|
| 2005/0161467 A1* | 7/2005 | Jones | A61M 15/009 222/23 |
| 2005/0247306 A1* | 11/2005 | Harvey | A61J 7/0481 128/200.21 |
| 2006/0084908 A1* | 4/2006 | Bonney | A61M 15/009 128/200.24 |
| 2008/0251551 A1* | 10/2008 | Huber | A61M 15/009 128/200.23 |
| 2008/0308102 A1* | 12/2008 | Davies | A61M 15/0086 128/203.15 |
| 2015/0174349 A1* | 6/2015 | Tunnell | A61M 15/009 128/200.14 |
| 2016/0256639 A1* | 9/2016 | Van Sickle | A61M 15/00 |
| 2017/0035976 A1* | 2/2017 | Sutherland | A61M 15/0068 |

* cited by examiner

RELEASABLE MONITOR WITH OPTICAL DOSE COUNTER FOR A MEDICAMENT INHALER

CROSS REFERENCE TO RELATED APPLICATIONS

This is a continuation-in-part application of U.S. patent application Ser. No. 15/247,776, filed Aug. 25, 2016, which is a continuation of U.S. patent application Ser. No. 13/705,813, filed Dec. 5, 2012, which is a continuation of U.S. application Ser. No. 12/381,145, filed on Mar. 6, 2009, which claims priority to New Zealand Patent Application No. 574666, filed Feb. 5, 2009, the contents of each of which are all hereby incorporated by reference in their entireties.

FIELD

Some embodiments relate to improvements in or relating to medicament inhalers. In particular, some embodiments relate to a device for releasable attachment to a medicament inhaler, which monitors patient usage of the medicament inhaler. Some embodiments may be particularly suitable for use with medicament inhalers used for the treatment of respiratory diseases such as asthma, COPD, cystic fibrosis, and bronchiectasis. However, it is to be understood and appreciated that the invention is not to be limited to such use. For example, the medicament inhalers could be used to supply medicaments to treat diseases such as diabetes, heart disease, and cancer. Furthermore, such medicament inhalers could also be used to supply pain medicament, or medicaments to treat disorders such as erectile dysfunction and nicotine addiction. The prior art and possible applications of the invention, as discussed below, are therefore given by way of example only.

BACKGROUND

The use of medicament inhalers for the treatment of diseases or disorders is well known. Such inhalers are generally referred to as Metered Dose Inhalers (MDI).

A common type of MDI is what is known as a pressurized Metered Dose Inhaler (pMDI). Such inhalers generally comprise a medicament canister and an actuator. The medicament canister contains medicament under pressure and is designed to deliver a metered dose of medicament in the form of an aerosol spray. The actuator generally comprises a substantially L-shaped hollow tube which has a first open end adapted to receive the medicament canister, and a second open end which acts as a mouthpiece.

Medicament canisters for use with a pMDI generally have a spray stem extending from one end which is adapted to engage with a spray-directing element housed within the actuator, and adjacent to the mouth piece of the actuator. When the canister is pushed down into the actuator, the spray stem and spray-directing element combine to direct a metered dose of medicament out through the mouthpiece and into the mouth of the user.

Another common type of MDI is what is known as a Dry Powder Inhaler (DPI). DPI's are generally in the form of a disc or grinder which may be rotated, or otherwise actuated, in order to dispense a metered dose of dry powder into an appropriate receptacle such as a mouthpiece. The dry powder may then be inhaled by the user, for example, by sucking strongly through the mouthpiece.

Further examples of medicament inhalers include delivery devices such as nebulizers and nasal sprays. Such delivery devices are generally designed to supply a dose of medicament in the form of a fine mist, which is directed either into the mouth or nasal cavity of a user.

Some medicament inhalers are kept on hand for use in a specific event or emergency. For example, if a person were to have a sudden asthma attack, they may reach for a medicament inhaler which contains what is generally known as a "reliever" medicament. A reliever medicament is fast acting and in most cases will relieve (or reduce the severity of) an asthma attack, almost instantaneously.

Other medicament inhalers are designed for regular use in order to prevent an event such as an asthma attack and/or to manage or control a disease such as asthma. Such inhalers are generally known as "preventers" because the regular use of such inhalers serves to prevent (or minimize the likelihood of) an asthma attack. The regular use of preventer medicament by asthma sufferers is generally effective in controlling the disease and/or preventing the vast majority of asthma attacks. Commonly, preventer medicament for asthma sufferers is taken twice a day, usually at a set time in the morning and in the evening.

There are now also available "combination" medicament inhalers which combine both a reliever and preventer medicament.

Studies have shown that many people overuse their reliever medicament, for example by using it when only mildly short of breath. The overuse of a reliever medicament has the potential to reduce the effectiveness of the medicament, which may render the medicament less effective in times of real need, for example during a severe asthma attack.

Moreover, a patient's increased use of a reliever medicament over a period of time may be indicative of a pending exacerbation event.

It would therefore be of advantage if there was available a device for monitoring patient usage of a reliever medicament inhaler in order to determine any potential overuse and/or for predicting a potential exacerbation event, prior to the event occurring.

A problem or difficulty associated with the use of preventer (or "combination") medicament inhalers is poor medicament compliance. That is, many studies have shown that users frequently do not take their medicament at the predetermined or prescribed times and/or in the required amounts.

The consequences of poor medicament compliance are reduced disease control, lower quality of life, lost productivity, hospitalization and avoidable deaths.

Not only is compliance to preventative medicaments typically low, but it has also been shown that actual compliance by a user is lower than the same user's estimated compliance.

In order to address these problems and difficulties, there are available a number of compliance monitoring devices for use with medicament inhalers.

Virtually all compliance monitoring devices incorporate dose counting means. In a general sense, dose counting means provide the simplest embodiment of a compliance monitor, as the dose count may indicate the number of medicament doses delivered and/or the number of medicament doses remaining in the medicament inhaler (the latter known as an "absolute dose counter"). The doses dispensed or remaining may also be displayed on a dosage counter, such as an LCD display, housed on the medicament inhaler.

The earliest dose counting mechanisms for pMDI's usually incorporated mechanical dose counting switch mechanisms such as levers or springs or trigger rods—which were mechanically actuated by movement of the canister within the actuator when a dose of medicament was dispensed. For example, see U.S. Pat. No. 4,817,822 (Rand et al) and U.S. Pat. No. 5,020,527 (Dessertine).

There are several problems associated with the use of such mechanical dose counting means. Firstly, the mechanical switch mechanisms include moving parts which may suffer wear and tear or otherwise deteriorate over time. Secondly, the switch mechanisms could break off and enter the medicament delivery pathway, and be inadvertently swallowed by the user. Thirdly, the mechanical switch mechanisms, which are commonly housed inside the actuator, can change the airflow characteristics of the inhaler, which may adversely impact on the medicament delivery performance of the inhaler. Lastly, mechanical switch mechanisms may be inadvertently triggered by the user, for example during washing of the actuator body to clean away any built up medicament residue (which must be done from time to time).

In recognition of some of the above problems or difficulties, U.S. Pat. No. 6,601,582 (Rand et al—but referred to herein as "GSK") describes a mechanical dose counter which is integrally formed on the medicament canister. However, a disadvantage associated with GSK is that the incorporation of a dose counting mechanism into each and every medicament canister adds cost to the end user. Moreover, given that each canister typically contains a one month supply of medicament, it is economically and environmentally wasteful to supply and then discard such technology with each month's medication.

More recent dose counting mechanisms incorporate electronic counting means. For example, see U.S. Pat. No. 5,544,647 (Jewettt et al), U.S. Pat. No. 6,202,642 (McKinnon et al) and US Patent Publication No. 2005/0028815 (Deaton et al).

However, most electronic dose counting mechanisms also rely on the canister physically engaging with a switch mechanism for the purpose of closing an electrical switch (to indicate a dosage count of one). For example, in order to record a dosage count of one, Jewett includes a microswitch (42) which is physically engaged by the leading edge (19) of a sleeve (17) which is attached to the canister (16)—see FIG. 1. Similarly, Deaton utilizes a ramp portion (42) which is physically engaged by the shoulder (26) of the canister (14) during the dispensing of a dose of medicament—see FIGS. 22a and 22b.

Hence, because such electronic dose counting means also include moving parts, these parts are likewise susceptible to wear and tear and/or deterioration over time (they may also be susceptible to breaking off and/or interfering with the airflow within the inhaler).

Furthermore, the fitting of mechanical or electronic dose counters to an inhaler usually requires modifications to the inhaler, for example the drilling of a hole in the side of the actuator or the attachment of a cap or sleeve to the canister. The fitting of such dose counters to an inhaler can therefore be a fiddly or time consuming operation.

More importantly however, any modifications made to the actuator (or canister) have the potential to interfere with the airflow characteristics within the actuator, possibly affecting the effectiveness of delivery of a dose of medicament. This may result in the patient not receiving the required amount of medicament in order to treat the disease.

Any modifications made to the actuator may also be prone to disruption when washing the actuator. This may subsequently result in inaccurate dose counting or compliance monitoring (Jewett and Deaton address this issue by housing the compliance monitoring means within a hermetically sealed housing—which increases cost and manufacturing complexity).

Most mechanical or electronic dose counters are designed to be absolute dose counters. That is, when a new medicament canister is placed in the actuator, the counters are either manually or automatically set to the number of doses remaining in the full canister (typically around 120 doses which usually comprises one month's supply of a preventer medicament). The GSK device referred to previously is an example of an absolute dose counter (but formed on the canister, rather than the actuator).

Every time a dose of medicament is dispensed, the dose counter serves to reduce the displayed number of doses remaining by one. Hence a user is able to keep track of the number of doses remaining in the canister, and can therefore ensure he/she has a replacement canister at hand prior to when the first canister is due to run out.

A disadvantage associated with absolute dose counters is that they are dedicated to only one canister at a time. Hence, they are not able to monitor the ongoing compliance characteristics of a user over a period of time which may involve the user going through many canisters of medicament. Moreover, absolute dose counters are not able to monitor a person's usage over all four seasons to determine useful information such as any seasonal fluctuations. Absolute dose counters are also not able to monitor the ongoing compliance characteristics of a user should they change medications when only half way through an existing canister.

Presently available electronic compliance monitoring devices also include means to record a range of compliance data, in addition to dose counting. For example, Dessertine includes a timer to indicate time between doses. McKinnon includes an electronic module to record date and time as well as more comprehensive patient usage information.

Most electronic compliance monitoring devices are integrally formed with the inhaler, usually by being mounted on, or integrally formed with, the actuator body (e.g., see Jewett and Deaton). This presents its own difficulties or limitations.

Firstly, because the compliance monitoring device is integrated with the medicament inhaler, it cannot generally be reused for longer than the life of the inhaler. Furthermore, compliance monitoring technology, and especially electronic compliance monitoring technology, adds cost when integrated into each and every inhaler.

However, reusing an actuator over more than one medicament canister can lead to residual medicament build-up that reduces the quantity of the drug delivered by the inhaler, and can also change the deposition properties of the aerosol particles, meaning patients get less medication.

Furthermore, repeatedly discarding the plastic and electronic compliance monitoring technology also creates an environmental sustainability problem that needs to be addressed. Additionally, as not all disease sufferers exhibit poor disease control or poor compliance, it is wasteful to provide such features embedded into each inhaler of a given type.

Perhaps partly in recognition of the above disadvantages associated with inhalers with integrally formed compliance monitoring means, McKinnon describes an electronic module which is releasably attachable to a sleeve which is fitted to the actuator. However, the removal of the electronic module from the sleeve renders the sleeve inoperable, which must then be removed and discarded, which is wasteful and expensive. Furthermore, the electronic module must be reprogrammed once it has been removed from the sleeve and prior to the module being fitted to another sleeve. Moreover, the fitting of the sleeve and electronic module to an inhaler is a time consuming and complex operation—which may present significant operational difficulties, especially for young children, the elderly or people of reduced mental capacity. Furthermore, the sleeve is preferably designed for attachment to only one specific brand of actuator. Hence, the McKinnon device cannot be used across a range of different actuators.

U.S. Pat. No. 5,564,414 (Walker et al) describes the concept of a removable sleeve designed to fit the body of a manufacturer's inhaler. However, Walker uses a mechanical counting mechanism (an external plunger-type trigger rod), which has the same disadvantages generally associated with mechanical counting means, as referred to previously.

PCT/US2008/052869 (Levy et al) describes a sleeve housing which is releasably attachable to an actuator body. The sleeve housing includes electronic monitoring apparatus and the device is designed to monitor usage in order to predict an exacerbation event. However, Levy relies on a counting means which requires attachment of a cap to the canister which is adapted to engage with a dose-dispensing sensor during the delivery of a dose of medicament. Hence, Levy requires modifications to the inhaler prior to being able to be used—which has the potential, over time, to interfere with the effectiveness of the inhaler to properly deliver medicament.

Levy also discloses the use of wireless technology to transmit compliance data to a remote device such as the laptop of a health professional. This data may be transmitted in real time or at predetermined set times.

Furthermore, the sleeve components described in McKinnon, Walker and Levy would not be able to be used in relation to a medicament canister already fitted with an absolute dose counter, eg the GSK device referred to previously.

Another problem associated with integrated electronic compliance monitoring devices is that many drugs are regulated and require exact actuator conformity. That is, there should be no modifications made to the actuator structure as any modifications may distort the reliability of the delivery of the medicament. Moreover, physicians, researchers, insurance companies, and so on, would not want to risk (for example, in terms of liability) the possibly of affecting the proper delivery of the medicament through these dedicated electronic instruments without the same assurance of proper drug delivery as with the commercial actuator provided by the drug manufacturer.

Having regard to the foregoing, it would therefore be of advantage if there was available a device for monitoring patient usage of a medicament inhaler which was releasably attachable to range of different medicament inhalers, and without any modifications being required to the inhaler.

BRIEF SUMMARY

It is an object of the present invention to provide an improved medicament inhaler which goes some way towards addressing the aforementioned problems or difficulties, or which at the very least provides the public with a useful choice.

It is a further object of the present invention to provide a releasably attachable device for a medicament inhaler which goes some way towards addressing the aforementioned problems or difficulties, or which at the very least provides the public with a useful choice.

Throughout this specification unless the text requires otherwise, the word 'comprise' and variations such as 'comprising' or 'comprises' will be understood to imply the inclusion of a stated integer or step or group of integers or steps but not the exclusion of any other integer or step or group of integers or steps.

Throughout this specification, the term "patient" or "user", when used in relation to a medicament inhaler, is to be understood to refer to any person that uses a medicament inhaler.

According to one aspect of the present invention, there is provided a device for monitoring patient usage of a medicament inhaler, said medicament inhaler being adapted to deliver doses of medicament, and wherein said medicament inhaler includes parts which move during the dispensing of a dose of medicament, wherein said device includes:
  a housing, said housing being releasably attachable to said medicament inhaler,
  an optical dose counter associated with said housing, said optical dose counter being adapted to determine when a dose of medicament has been dispensed by transmitting optical signals through the medicament inhaler,
  an electronic control module associated with said housing, said electronic control module including, or being in communication with, said optical dose counter,
  said electronic control module being adapted to monitor and/or store data relating to patient usage of said medicament inhaler,
  the arrangement and construction being such that said device is attachable to said medicament inhaler, and subsequently operable, without any modifications being required to be made to said medicament inhaler.

The medicament inhaler may be any suitable medicament inhaler capable of delivering a dose(s) of medicament, and preferably (but not exclusively) a metered dose of medicament. For example, the medicament inhaler may be a pMDI, a DPI, a nebulizer or a nasal spray.

Preferably, the medicament inhaler may include part(s) which move during the delivery of a dose of medicament. For example, in the case of a pMDI, the moving part would be a medicament canister, which moves within an actuator during the dispensing of a dose of medicament. Likewise, a DPI may include a rotating disk, which moves in order to place a dose of dry medicament into a compartment, for subsequent inhalation by the patient.

The device may be utilized for use with inhalers that contain a preventer medicament and/or inhalers that contain a combination medicament. The device may therefore serve as a compliance monitor in respect of the patient usage of such inhalers.

The device may also be used to monitor patient usage of a reliever medicament in order to determine any potential overuse and/or for predicting a potential exacerbation event, prior to the event occurring.

The device may preferably include a housing which may be releasably attachable to an inhaler.

An advantage associated with having a releasably attachable housing is that the device may be reused by the patient. For example, when an inhaler exhausts its supply of medicament, the device may be removed from the inhaler and releasably fitted to either another inhaler or the device may remain on the same inhaler, but with a replacement supply of medicament added. Furthermore, any data being collected by the device in relation to the patient usage of the inhaler may therefore be continuous over a period of time that may include the patient going through many supplies of medicament (either with the same inhaler or across a range of inhalers and/or medicaments). Hence, a comprehensive amount of patient usage data may be obtained over a significant period of time.

The releasably attachable housing may preferably be attachable to the inhaler, and subsequently operable, without any modifications being required to the inhaler. That is, the inhaler simply sits partially or fully within the housing of the device.

A significant advantage of such an arrangement is that the device does not in any way interfere with, or otherwise affect, the ability of the inhaler to administer medicament. This compares favorably with the prior art devices referred to previously, most of which require modifications to the inhaler in order to be fitted and/or operable. For example, modifications may include the drilling of a hole into the side of the inhaler or the fitting of a cap to a medicament canister—both of which have the potential to interfere with the airflow characteristics within the inhaler and/or adversely affect the ability of the inhaler to dispense medicament.

Furthermore, the attaching of the housing to the inhaler preferably does not require the use of any tools in order to be fitted (for example, the housing is not releasably screwed into or onto the inhaler). Instead, the inhaler to be used with the present invention is simply placed within the housing of the device.

The housing may be of any suitable size, shape or configuration as required or desired, or as dictated by the type or configuration of the inhaler.

In one embodiment, the housing may be in the form of a sleeve adapted to be fitted around the outside of the inhaler.

The housing may be adapted to partially enclose the inhaler and/or to clip onto the inhaler. For example, the housing may be in the form of a substantially U-shaped sleeve adapted to clip snugly around the outside of the inhaler. In such an embodiment the housing may be provided with additional means to help secure the housing to the inhaler, for example by the use of ties, straps or clips.

In another embodiment, the housing may be adapted to fully encircle and/or fully contain the inhaler.

The housing may be provided with a hinged portion, which, when open, allows the inhaler to be placed within the housing, and which, when closed, serves to retain and/or secure the inhaler substantially within the housing. In such an embodiment, the hinged portion may be provided with closure and release means, to secure the hinged portion in a closed position, and release the hinged portion from said closed position, respectively. For example, the closure and release means may be provided by a suitable fastener such as a VELCRO brand fastener, or alternatively by a latch-type mechanism. The closure and release means may also be provided by the closing edge of the hinged portion having a male portion which is adapted to releasably engage with a corresponding female portion formed in the housing proper.

The housing may be made of any suitable material although a plastics material may be preferred as it is relatively light, and may be conveniently and inexpensively mass produced, for example by injection molding technology.

The housing may be substantially opaque, translucent or transparent. For example, the housing may be substantially opaque and of the same color as a particular manufacturer's range of inhalers to which it is intended to be fitted.

Alternatively, the housing may be substantially transparent (or translucent). This may have practical implications given that the inner working of the housing and/or the inhaler may be inspected or monitored through the housing. Such an embodiment may also have some aesthetic appeal given that the inner workings of the housing may be viewed.

The optical dose counter may preferably be adapted to determine when a dose of medicament has been dispensed by transmitting optical signals through the inhaler.

Preferably, the optical dose counter transmits (and receives) optical signals from a position outside of the inhaler. Hence, the optical dose counter does not impact, in any way, on the ability of the medicament inhaler to dispense medicament.

Preferably, the optical dose counter may be incorporated within the housing of the device. Alternatively, the optical dose counter may be housed on the outside of the housing.

An advantage of utilizing an optical dose counter generally is that the dose counter does not require any physical connection with the medicament inhaler in order to be able to register when a dose has been dispensed. Furthermore, the recording of a dose of medicament does not require any moving parts such as mechanical or electrical switches.

The optical dose counter may utilize any type of light from within the electromagnetic spectrum. For example, the dose counter may utilize infrared light. Alternatively, the dose counter may utilize visible light.

According to another aspect of the present invention there is provided a device for monitoring patient usage of a medicament inhaler, substantially as described above, wherein said optical dose counter includes:
 at least one light transmitter able to transmit an optical signal,
 at least one light receiver able to receive an optical signal,
 the arrangement and construction being such that movement of the part(s) within the medicament inhaler during the delivery of a dose of medicament alters the optical signal(s) whereby the optical dose counter is able to determine that a dose has been dispensed.

In one embodiment, the light receiver(s) may be positioned substantially opposite the light transmitter(s) in order to receive a substantially direct beam of light, for example a laser beam. In such an embodiment, the movement of part(s) within the inhaler during the dispensing of a dose may temporarily block the beam of light, thus enabling the dose counter to register that a dose of medicament has been dispensed.

In an alternative embodiment, the light transmitter(s) may transmit a normal beam of light, which will generally disperse outwardly from the point of transmission. The movement of part(s) within the inhaler during the dispensing of a dose will therefore affect the light signal, for example by the light reflecting off the part(s) as they move. This will alter the intensity of light being received by the light receiver(s), thus enabling the dose counter to register that a dose of medicament has been dispensed. In such an embodiment, it is not necessary that the moving part(s) actually block the light signal to enable a dose to be detected and/or counted. Hence, the light transmitter(s) and light receiver(s) need not necessarily be positioned substantially opposite each other. It is also possible that the light transmitter(s) and light receiver(s) could be positioned next to each other or side by side.

One skilled in the art will appreciate that the sensitivity of the optical dose counter could be calibrated to ensure that the optical counter only registers when a dose has been dispensed, as compared to other instances of movement of the part(s) within the inhaler, for example any movement caused when the inhaler is bumped or being carried around in the bag of a user.

The device may also include an audio sensor to detect sound associated with movement of the medicament container during delivery of a dose and/or sound associated with the inhalation of the medicament by the patient. In such an embodiment, the optical dose counter may be adapted to receive information gathered by the audio sensor, and use this to confirm its own data that a dose of medicament has been dispensed. Furthermore, the optical dose counter may be configured to only record that a dose has been dispensed when the optical dose sensor and the audio sensor both determine that a dose has been dispensed. That is, if the audio sensor determined that a dose had been dispensed, but the optical dose counter did not (or vice versa), then a dose may not be recorded.

It is also envisaged that the optical dose counter may be adapted or able to monitor for non-dose counting events, for example:

When a medicament container has been removed from and/or placed into the inhaler.

When an inhaler has been removed from and/or placed into the housing of the device.

The amount of medicament remaining in the medicament container.

For items 1 and 2 above, the removal of the medicament container or inhaler will affect the light signal, for example by the light reflecting off the part(s) as they move. This will alter the intensity of light being received by the light receiver(s), thus enabling the optical dose counter to register and/or record that one or both of these events has occurred. Moreover, the removal of the medicament container will alter the light intensity in a different way to the removal of the inhaler proper, and hence the optical dose sensor may be calibrated be able to differentiate between these two events and/or determine which event has occurred.

For item 3 above, the optical dose counter may be able to determine the amount of medicament remaining in the medicament container by monitoring the ongoing intensity of light passing through the medicament container. The optical dose counter and/or electronic control module may be further adapted to sound an alert when the level of medicament remaining reaches a certain threshold.

The optical dose counter may also be provided with its own memory (and real time clock) in order to store any counting or non-counting data.

The electronic control module may preferably be housed within the housing of the device. Alternatively, the electronic control module may be housed on the outside of the housing.

The electronic control module may preferably include, or be in communication with the optical dose counter. Hence, the optical dose counter may be a standalone unit in communication with the electronic control module, or it may be deemed to be incorporated within the electronic control module.

It is envisaged that both the optical dose counter and/or electronic control module may be housed within a hermetically sealed compartment(s), for example to minimize exposure to dust or medicament particles or to enable the device to be washed from time to time.

The electronic control module may preferably include, or be in communication with, means for monitoring and/or storing data relating to patient usage of the medicament inhaler. The means for storing data may, for example, include a ROM or RAM memory storage means.

The electronic control module may further include processing means to enable the electronic control module to perform operations on the patient usage data. The result of any operations performed on the patient usage data may be stored in the memory associated with the electronic control module.

The electronic control module may preferably include a user interface to allow the patient to access any data recorded or received by the electronic control module, and/or to change the settings of the device. Preferably, the user interface may include a visible screen, such as a LCD screen, and at least one control button.

The electronic control module may preferably include a dose counter display for viewing by the patient, for example on a LCD screen. This LCD screen may be the same as that used with the user interface. In such an embodiment, the dose counter display may temporarily disappear when the patient is using the user interface to change the settings of the device, only to reappear once the patient has finished, for example after a predetermined length of time has passed since the user interface was last used.

Alternatively the dose counter display may have its own dedicated display.

Preferably, the dose counter display may be updated each time a dose of medicament is dispensed.

The device may be used by the patient to serve as an absolute dose counter. In such an embodiment, and for example, the patient may utilize the user interface to choose this option and then enter the total number of doses remaining to be dispensed by the medicament, this number being displayed by the dose counter display. After the dispensing of each dose of medicament by the inhaler, the dose counter display will reduce the number of doses remaining by one.

The device may also be used by the patient to serve as a non-absolute dose counter. In such an embodiment, and for example, the patient may utilize the user interface to choose this option and then reset the dose counter display counter to zero. After the dispensing of each dose of medicament by the inhaler, the dose counter display will increase the number of doses taken by one. Furthermore, the patient may keep an ongoing total of the number of doses of medicament dispensed over a set period of time, and in relation to a number of medicament containers, rather than just in relation to one supply of medicament.

Preferably, the electronic control module includes, or is in communication with, a means to record the date and/or time of each dose of medicament, for example a real time clock. Furthermore, the real time clock may also be used to date/time stamp any other events, for example when the processor performed certain operations, or when an alarm was raised or sent, or when the inhaler was removed from the device, and so on.

The electronic control module may preferably include notification means to notify the patient of a particular event. For example, the notification means may include a means for reminding the patient to take a dose of medicament should the electronic control module determine or receive notification that the patient has not taken a dose within a predetermined time. Likewise, the notification means may be adapted to alert the patient to a situation where they have taken too much of a medicament over a predetermined time period, which may be indicative of an exacerbation event.

The notification means may preferably include, or be in communication with, a visual display and/or an audio output means.

For example, a visual notification display may appear on the user interface, perhaps as a flashing message to draw attention to itself. Alternatively, or additionally, an audio output such as an alarm may be made through the audio output means. Different alarms may be sounded for different alerts, or if a patient has continually forgotten to take his/her medicament. In such an embodiment, it may also be possible for the patient to mute the audio output means, for example if the patient was in a meeting or a movie theatre.

A further example of a notification means that may be used with the present invention is that described in our granted NZ Patent No. 540250.

The electronic control module may preferably include, or be in communication with, a wireless transmitter to enable the wireless transmitting of patient usage data. The data may preferably be transmitted to a public access network such as the internet. Alternatively, the data may be transmitted to a private access network such as dedicated computer or intranet.

The wireless transmitter may preferably be in the form of a cell phone chip housed within the electronic control module (or the housing). An advantage associated with the present invention is that the significant cost of installing a cell phone chip may be mitigated by the fact that the device is reusable and has an indefinite lifetime. That is, one reason cell phone chips (or like wireless technology) are not usually included in presently available monitoring devices is because such monitoring devices are not designed to be reusable, and hence the cost of installing a cell phone chip in such a short-lived, disposable device is prohibitive. The present invention therefore overcomes this problem because the device is designed to be reusable over a significant time period, and across a range of different inhalers.

The wireless transmitter may preferably be adapted to transmit data to a third party such as a medical practitioner or to a parent or care giver.

The wireless transmitter may preferably be adapted to transmit the data in real time.

Alternatively, the wireless transmitter may be adapted to transmit data at a predetermined time(s), or in response to when a predetermined condition eventuates. For example, if too many doses of medicament have been dispensed over a set time period this may be indicative of an impending exacerbation event. An appropriate warning may then be made to either the patient or a third party such as a care giver or medial practitioner. Likewise, if the patient has forgotten to take their medicament a certain number of times and over a predetermined length of time, an appropriate warning may likewise be transmitted to such a third party.

The electronic control module may also preferably include, or be in communication with, a wireless receiver (or transceiver) to enable the wireless receipt of data or instructions. In such an embodiment, and for example, the wireless receiver may be utilized to enable the patient (or a third party) to send instructions from a remote location or electronic device to change one or more of the settings of the device, or to access the data stored within the device. Such an embodiment may provide an alternative to the patient using the user interface and/or may enable the patient to have more options regarding the choice of (or change to) settings of the device. The wireless receiver may also be utilized to receive notifications and possibly sound an alert or alarm. For example, if a third party such as a parent or medical practitioner had received data from the device which indicated that an exacerbation was imminent, that third party may be able to transmit a warning to the device, for example by the use of a laptop or mobile phone.

The device may alternatively, or additionally, be provided with a wired port to enable the transmission of data or instructions between the device and another electronic device.

The optical dose counter may be adapted to determine deterioration in the inner surfaces of the medicament inhaler, for example deterioration caused by buildup of medicament residue, which should be cleaned off to ensure the ongoing optimal performance of the inhaler. The means for determining this may be based on changes in the light levels reflected from the inner surfaces of the medicament inhaler over time. Namely, the light transmitter(s) of the optical dose counter will be continuously transmitting light through the inhaler when the medicament inhaler is in its rest position, that is, in a non-dose dispensing configuration. Over time, the light receiver(s) may detect a slight variation in the quality of light reflected off the inside walls of the inhaler, which may suggest the inhaler may need to be cleaned and/or replaced once a predetermined variation has been reached. One such a predetermined variation has been reached, an audible or visual alarm may be instigated to alert the patient to the deteriorating condition of the inhaler.

It may be appreciated that the device, which is the subject of the present application, may be utilized across a range of different medicament inhalers of similar design. For example, the device may be designed whereby it was able to be used across a certain range (such as one company's range) of pMDI or DPI inhalers which were of similar size and/or which shared similar design features. Hence, a patient may be able to utilize the device for ongoing usage monitoring or compliance if, for example, they changed medicament (which came with a different inhaler), but whereby the different inhaler was still able to be utilized with the device. This may be of particular advantage during clinical trials where the ongoing monitoring of a patient is being undertaken over a considerable time period, and perhaps whereby the patient changes medicament half way through the trial.

The device may also be adapted to be operationally effective when attached to a medicament inhaler which already includes an inbuilt dose counter, for example the GSK device referred to previously. In such an embodiment, the housing of the device may be provided with cut away portions so that the inbuilt dose counter may still be viewed.

The description of a preferred form of the invention to be provided herein, with reference to the accompanying drawings, is given purely by way of example and is not to be taken in any way as limiting the scope or extent of the invention.

DETAILED DESCRIPTION

Figure 2:
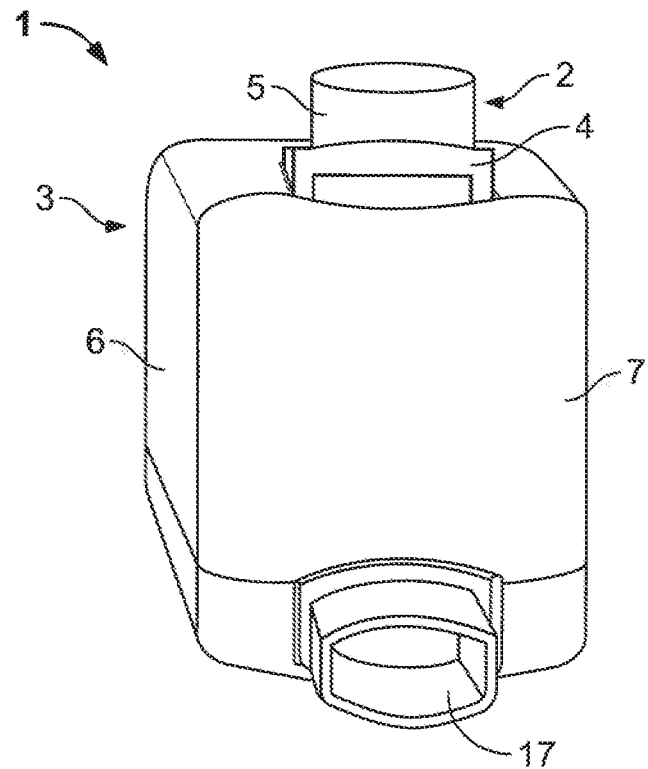
FIG. 2 is a front perspective view of the embodiment illustrated in FIG. 1, when attached to a pMDI medicament inhaler.

Having regard to the drawings, there is shown a device, generally indicated by arrow 1, for monitoring the patient usage of a medicament inhaler, generally indicated by arrow 2 (see FIG. 2).

The device 1 includes a housing, generally indicated by arrow 3, for releasable attachment to the inhaler 2. The housing 3 is adapted to fully encircle and/or fully contain the inhaler 2.

The inhaler 2 is a pMDI inhaler which includes an actuator 4 and a medicament canister 5.

The housing 3 is comprised of an injection molded plastics material and is substantially translucent in appearance.

The housing 3 is provided with a main body portion 6 and a hinged body portion 7.

The main body portion 6 is substantially hollow and includes an interior portion 8 which is adapted to substantially match the exterior configuration of the inhaler 2, whereby the inhaler 2 may be snugly retained within the interior portion 8 of the main body portion 6. The main body portion 6 also includes lower ledge portions 9, upon which the underside 10 of the actuator 4 rests, once the inhaler 2 has been placed within the main body portion 6.

Figure 1:
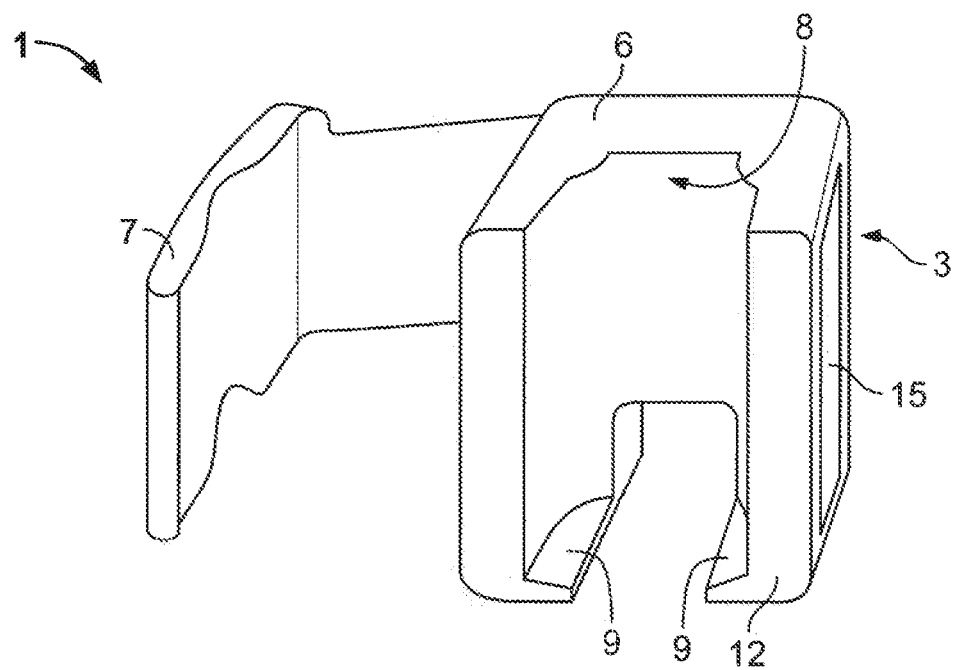
FIG. 1 is a front perspective view of one possible embodiment of the present invention.

The hinged portion 7 in FIG. 1 is shown in an open position which allows the inhaler 2 to be placed into the interior portion 8 of the main body portion 6. Once the inhaler 2 has been placed in the main body portion 6, the hinged portion 7 is closed, as shown in FIG. 2. The hinged portion 7 is releasably secured to the main body portion 6 by the use of a latch (not shown).

It may be seen from the drawings that the housing 3 is releasably attachable to, or around, the inhaler 2, and subsequently operable, without any modifications being required to the inhaler 2. The inhaler 2 may be operated as normal once retained within the device 1.

Furthermore, the attaching of the housing 3 to or around the inhaler 2 does not require the use of any tools in order to be fitted; instead the inhaler 2 is simply placed within the housing 3 of the device 1.

The device 1 includes an electronic control module 11 (not physically shown, but represented in FIG. 10) housed within a side 12 of the housing 3. The electronic control module 11 is adapted to monitor and/or store data relating to patient usage of the inhaler 2.

The side 12 of the housing 3 includes a user interface, generally indicated by arrow 13. The user interface 13 allows the patient to access data recorded or received by the electronic control module, and also to change the settings of the device 1. The user interface 13 includes operational buttons 14 and a LCD display 15. One of the operational buttons 14 may be an on/off switch.

Figure 4:
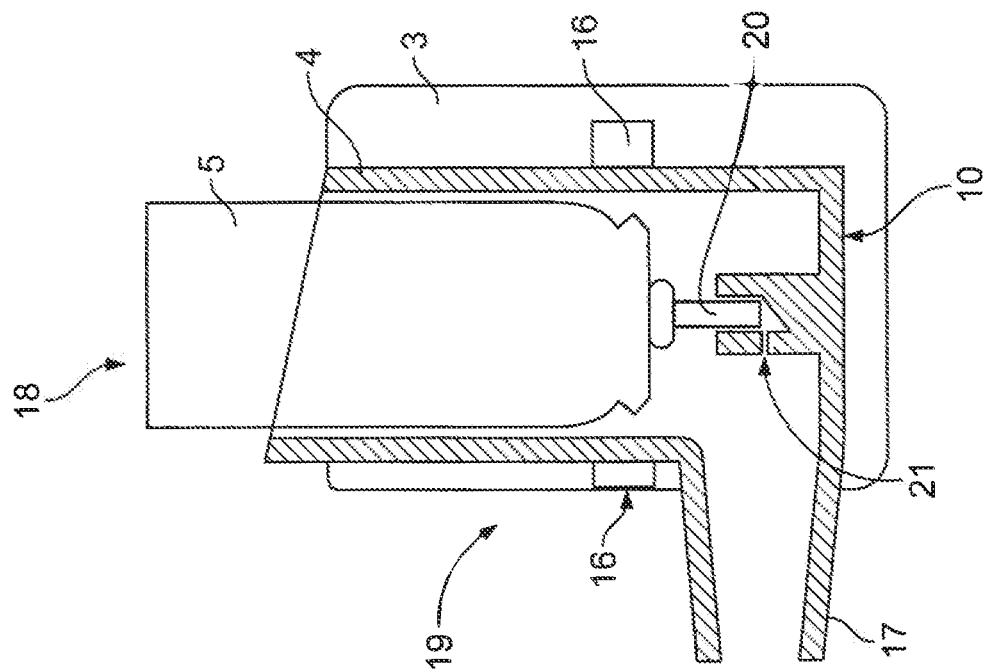
FIG. 4 is a cut-away view of the embodiment illustrated in FIG. 3.

The device 1 includes an optical dose counter, generally indicated by arrow 16 (see FIG. 4). The optical dose counter 16 is housed within the housing 3, and is in electronic communication with the electronic control module 11 (see FIG. 10). The optical dose counter 16 is adapted to determine when a dose of medicament has been dispensed by the inhaler 2, by transmitting optical signals through the inhaler, 2, and from a position outside of the inhaler 2 (the operation of the optical dose counter 16 is described in more detail later).

Having regard to FIG. 4, the medicament canister 5 includes a spray stem 20, which is adapted to engage with the spray-directing element 21 formed integrally within the actuator 4.

When a patient wishes to dispense a dose of medicament, he/she places their mouth over the mouthpiece 17 of the actuator 2, and presses down on the top 18 of the medicament canister 5—in the direction shown by arrow 19. This has the effect of pushing the spray stem 20 into the spray directing element 21, which releases a metered dose of medicament, and which is directed out of the mouthpiece 17 and into the mouth of the patient. The patient will generally inhale deeply at the same time that the medicament is dispensed so that the medicament is inhaled into the lungs of the patient.

Figure 5:
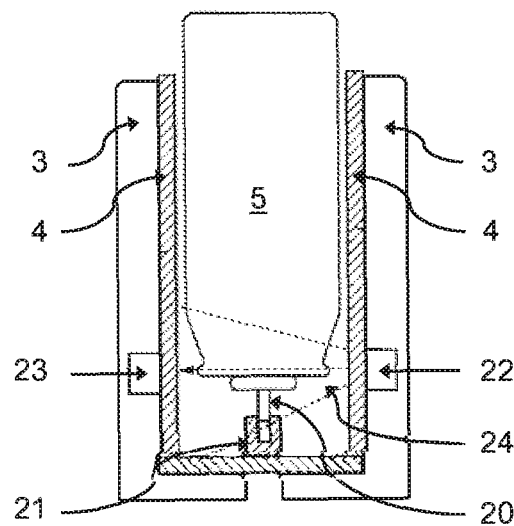
FIG. 5 is cut away view illustrating one possible embodiment of an optical dose counter for use with the present invention, when a medicament canister is in a rest position.
Figure 6:
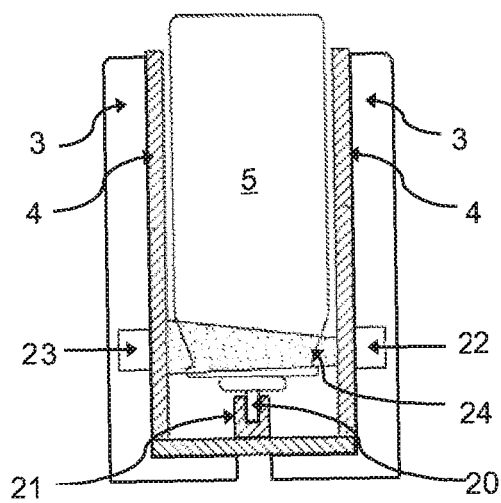
FIG. 6 is a view of the embodiment illustrated in FIG. 5, with the medicament canister in a dose dispensing position.

FIGS. 5 and 6 show the operation of the optical dose counter 16.

FIG. 5 shows the canister 5 in the non-dispensing, or rest position, whereas FIG. 6 shows the canister 5 in the position it would be when dispensing a dose of medicament.

Having regard to FIG. 5, it may be seen that the optical dose counter 16 includes a light transmitter 22 housed within the housing 3 on one side of the actuator 4, and a light receiver 23, housed within the housing 3 on the opposite side of the actuator 4.

The light transmitter 22 is adapted to constantly transmit a beam of infrared light 24, which disperses outwardly from the point of transmission, as shown. An alternative arrangement may be to have the light transmitter 22 transmit a strobe.

The outwardly dispersing nature of the beam of light 24, occurs naturally, but this may also be accentuated by diffraction caused by the beam of light 24 passing through the outside of the actuator 4.

The light transmitter 22 may preferably transmit a continuous beam of light 24.

The light receiver 23 is constantly monitoring receipt of the beam of light 24 from the light transmitter 22. In a preferred embodiment, the light receiver may take a reading of the beam of light 24 approximately 30 times per second. Alternatively, other reading times may be utilized so long as the readings are frequent enough to detect movement of the canister 5 during the dispensing of a dose of medicament—the movement time of the canister (or dispensing time) is typically around 100 milliseconds.

When the canister 5 is in the rest position, as shown in FIG. 5, the canister 5 remains immobile within the actuator 4. The characteristics (such as intensity and direction) of the beam of light 24, as it passes through the actuator 4, are therefore not affected in any significant way. The light receiver 23 constantly monitors this.

However, when a dose of medicament is dispensed by the canister 5, as shown in FIG. 6, the movement of the canister 5 within the actuator 4 has the effect of changing the characteristics of the beam of light 24, and this is noted by the light receiver 23—and hence the optical dose counter 16 is thus able to determine that a dose has been dispensed.

The optical dose counter 16 is electronically connected to the electronic control module 11 (see FIG. 10), so that data relating to the dispensing of doses by the optical dose counter 16 may be communicated to the electronic control module 11, where it may be stored in memory, and also have other patient usage data associated with it, for example, date and time.

It may be seen from FIGS. 5 and 6 that the optical dose counter 16 is able to determine when a dose of medicament has been dispensed without impacting in any way whatsoever on the operation of the inhaler 2 or on the medicament delivery channel (namely the inside of the actuator 4 and mouthpiece 17). This is because the optical dose counter 16 is housed within, and operable from, a position outside of the actuator 4. Furthermore, the use of light to record the dispensing of a dose is non-intrusive, and does not involve or require any physical connection whatsoever with the moving parts (canister 5 and spray stem 20) within the actuator 4 during the dispensing of a dose. This is a significant advantage of the present invention over and above the prior art devices referred to previously.

Figure 10:
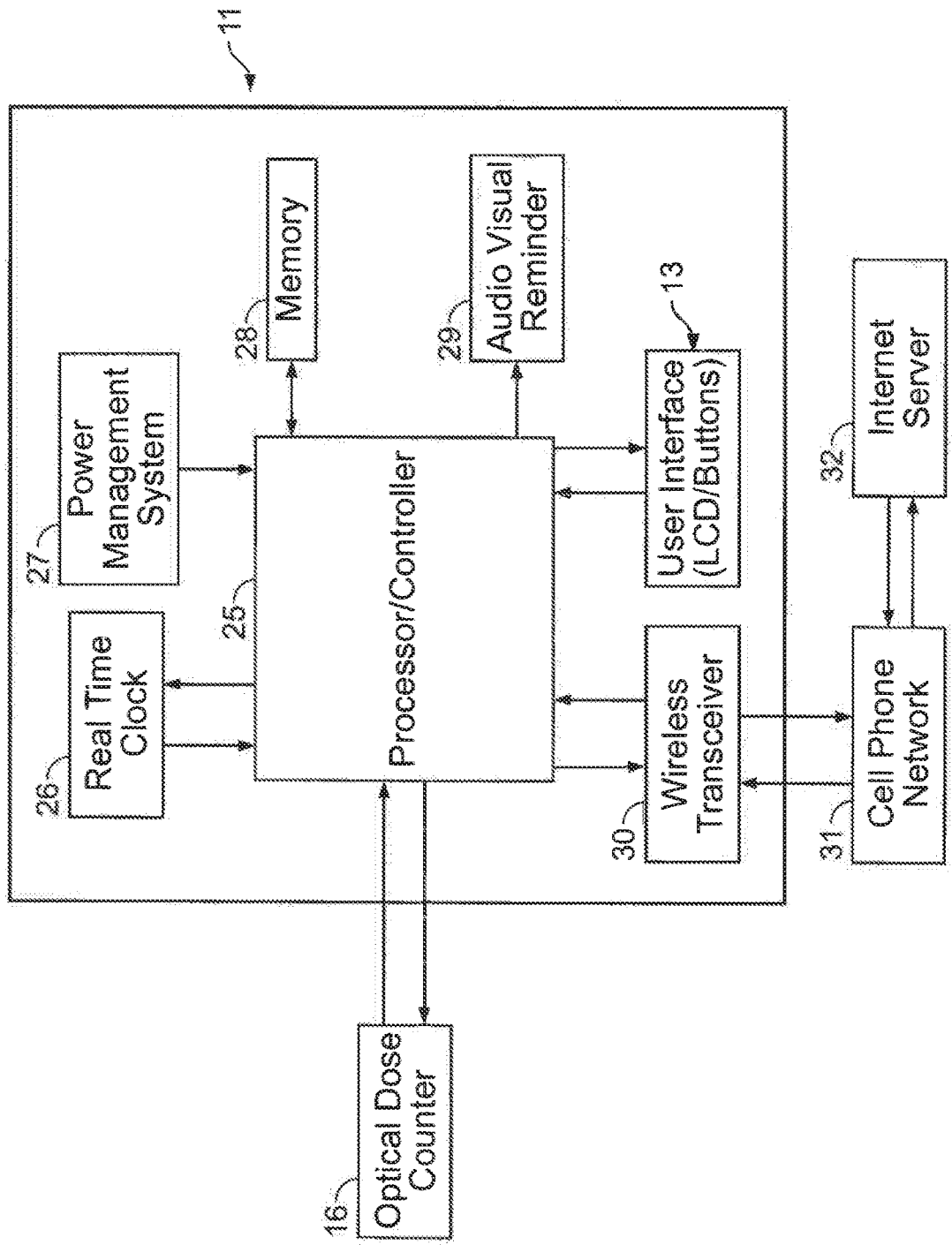
FIG. 10 is a simplified system block diagram showing one possible embodiment of an electronic control module and optical dose counter for use with the present invention.

The electronic control module 11 is represented in the simplified system block diagram of FIG. 10.

The electronic control module 11 includes a central processor/controller unit 25. The processor/controller unit 25 is adapted to control and manage the overall operation of the device 1, as well as being responsible for processing or performing operations on the data.

For example, the electronic control module may be able to monitor and/or record the date/time of events such as the opening and/or closing of the hinged portion 7 of the housing 3; the replacement of the battery; when any alarm notifications were made and whether the patient received them or responded to them; when a canister has been removed and/or replaced, and so on.

The electronic control module 11 is in electronic communication with the optical dose counter 16, as shown in FIG. 10.

The electronic control module 11 includes a real time clock 26, which is able to note the date and time of each dose of medicament dispensed by the inhaler 2. Furthermore, the time may be displayed on the LCD display 15, if required.

The electronic control module 11 includes a power management system 27. The power management system 27 includes a battery (not shown), and may also include warning features whereby if the battery is getting low, the patient maybe alerted to this. The battery may be a replaceable battery or a rechargeable battery.

The electronic control module 11 includes a memory 28 for storing patient usage data, or any other data relating to the use of the device 1. The memory, for example, may be RAM and/or ROM.

The electronic control module 11 includes a notification means which includes an audio/visual output 29. The audio output is in the form of a small speaker (not shown) and the visual output is in the form of a second small LCD screen (also not shown).

The audio/visual output 29 is in communication with the central processor/controller 25 and is adapted to notify the patient of a particular event. For example, audio/visual output 29 may sound an alarm to remind the patient to take a dose of medicament should it be determined that the patient has not taken a dose within a predetermined time. Likewise, the audio/visual output 29 may be adapted to alert the patient to a situation where they have taken too much of a medicament over a predetermined time period, which may be indicative of an exacerbation event. Furthermore, the notification means and audio/visual output may combine to sound alerts for any particular event, such as a dose having been recorded (a beep may sound for example), the dose counter reaching a predetermined number, and so on.

Figure 3:
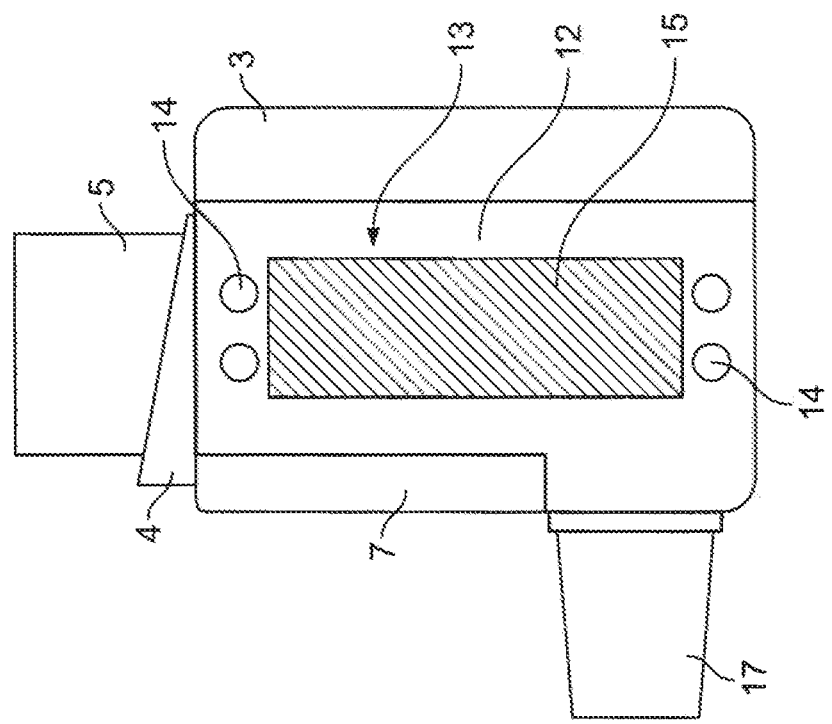
FIG. 3 is a side view of the embodiment illustrated in FIG. 2.

The electronic control module 11 includes a user interface 13, which includes operational buttons 14 and a LCD screen 15 (see FIG. 3). The patient may utilize the user interface to change the operational settings of the device 1.

The electronic control module 11 includes a wireless transmitter and receiver to enable the wireless transmitting and receiving of data or instructions. The wireless transmitter/receiver is an integrated component and is represented as a transceiver 30 in FIG. 10. The transceiver 30 is essentially a means to allow the device to operate interactively (ie, two-way) with any number or type of outside electronic devices, for example a cell phone (via a cell phone network) or laptops (via an internet server).

The wireless transceiver 30 is in the form of a cell phone chip (not shown) housed within the electronic control module 11 (or the housing 3). The significant cost of installing a cell phone chip is mitigated by the fact that the device 1 is reusable and has an indefinite lifetime.

The wireless transceiver 30 is able to transmit data to a third party or to another electronic device. For example, the wireless transceiver 30 may transmit patient usage data to a medical practitioner or to a parent or care giver. It may do this by transmitting the data to a cell phone network 31, and subsequently to an internet server 32 (and therefore to a mobile phone or laptop respectively).

The wireless transceiver 30 is also adapted to transmit the data in real time. Alternatively, the wireless transceiver 30 may be adapted to transmit data at a predetermined time(s), or in response to when a predetermined condition eventuates, for example if too many doses of medicament have been dispensed in a set time period indicating that an exacerbation event may be imminent. An appropriate warning may then be made to either the patient or a third party such as a parent or medial practitioner.

The transceiver 30 is also able to wirelessly receive data or instructions. For example, the transceiver 30 may be utilized to enable the patient (or perhaps a third party) to send instructions from a remote location or electronic device to change one or more of the settings of the device 1. The transceiver 30 may also be utilized to receive outside instructions to sound an alert or alarm. For example, if a third party such as a parent or medical practitioner had received data from the device 1 which indicated that a exacerbation was imminent, that third party may be able to transmit a warning to the device 1, for example by the use of a laptop or mobile phone.

The LCD screen 15 may be utilized, if required, as a dose counter display, for example for displaying the number of doses of medicament remaining in the canister 5, or alternatively for displaying the number of doses taken by the patient over a set time period.

Preferably, the dose counter display may be updated each time a dose of medicament is dispensed.

The device 1 may be used by the patient to serve as an absolute dose counter. For example, the patient may utilize the user interface 13 to choose this option and then enter the total number of doses remaining to be dispensed by the medicament canister 5—with this number then being displayed by the dose display counter on the LCD screen 15. After the dispensing of each dose of medicament by the inhaler 2, the dose counter display will reduce the number of doses remaining by one.

The device 1 may also be used by the patient to serve as a non-absolute dose counter. For example, the patient may utilize the user interface 13 to choose this option and then reset the dose display counter to zero. After the dispensing of each dose of medicament by the inhaler 2, the dose counter display will increase the number of doses taken by one. Because the device is reusable across a range of medicament inhalers 2 or canisters 5, the patient may keep an ongoing total of the number of doses of medicament dispensed over a set period of time, rather than just in relation to one supply of medicament.

Figures 7, 8:
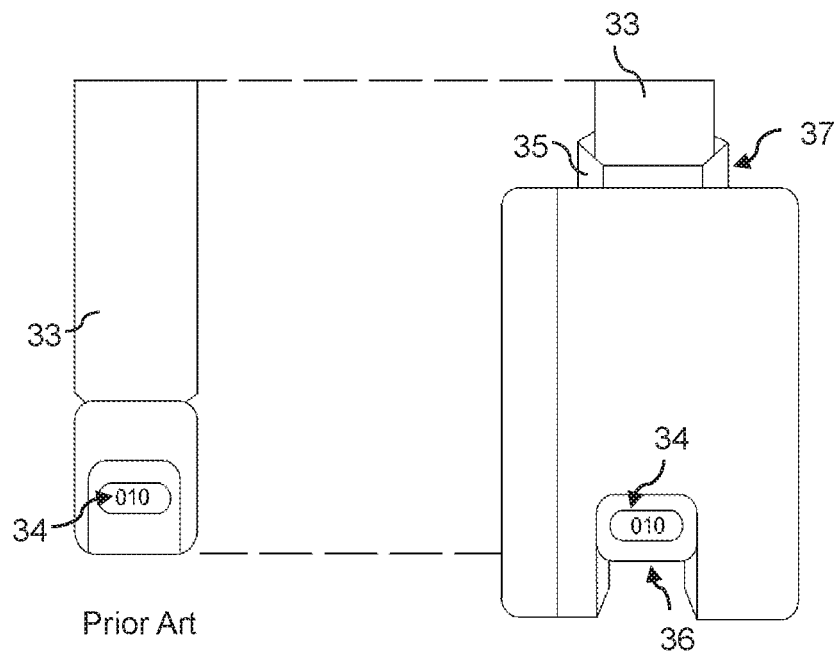
FIG. 7 is a rear view of a prior art medicament canister.
FIG. 8 is a rear view of the prior art medicament canister illustrated in FIG. 7, when housed within the embodiment illustrated in FIG. 1.

FIGS. 7 and 8 illustrate how the device 1 may be utilized with a prior art inhaler 37 which has a medicament canister 33 with an inbuilt mechanical dose counter. The prior art inhaler 37 is the GSK prior art device referred to previously. The canister 33 includes an absolute dose counter display 34—which indicates that there are 10 doses remaining in the canister 33. The canister 33 is adapted to fit within its own dedicated actuator 35.

FIG. 8 shows the device 1 from the rear, and with the prior art inhaler 37 housed within the housing 3 of the device 1. The housing 3 is provided with a cut-away portion 36 which enables the dose counter display 34 to be viewable once the prior art inhaler 37 has been placed within the housing 3 of the device 1. An advantage associated with such an embodiment is that the prior art inhaler 37 may continue to function as an absolute dose counter with respect to the current canister of medicament 33. Furthermore, the device 1 may be utilized by the patient to act as a non-absolute dose counter (as described above), and for a length of time covering the use of many canisters 33. Hence, the patient may obtain two useful sets of data—one relating to the patient usage in relation to each canister 33 of medicament, and the second relating to general usage information over a significant (or predetermined) length of time.

Figure 9A:
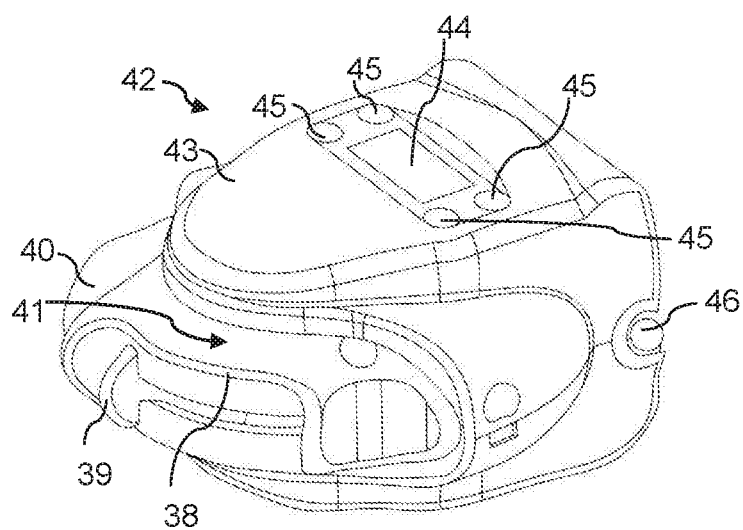
FIG. 9A is a perspective view of another possible embodiment of the present invention, when attached to a DPI medicament inhaler.
Figure 9B:
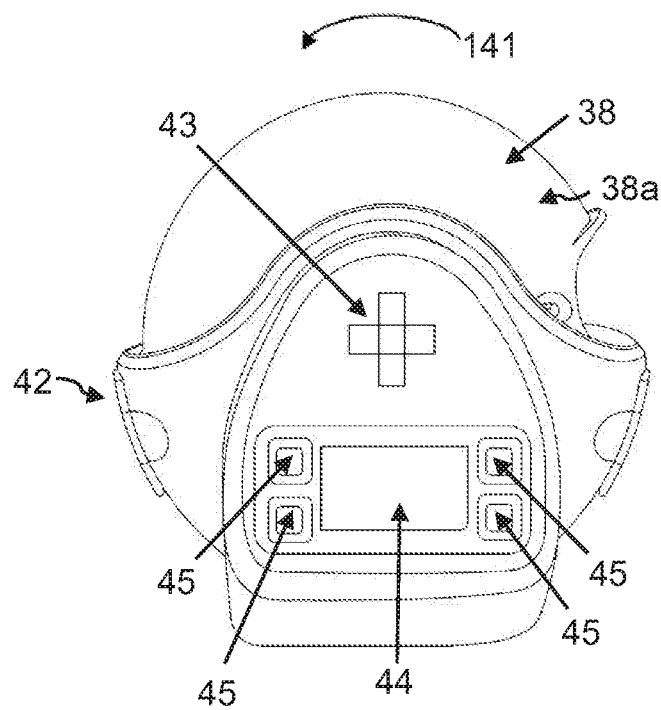
FIG. 9B is front view of a DPI medicament inhaler housed within the embodiment illustrated in FIG. 9A.
Figure 9C:
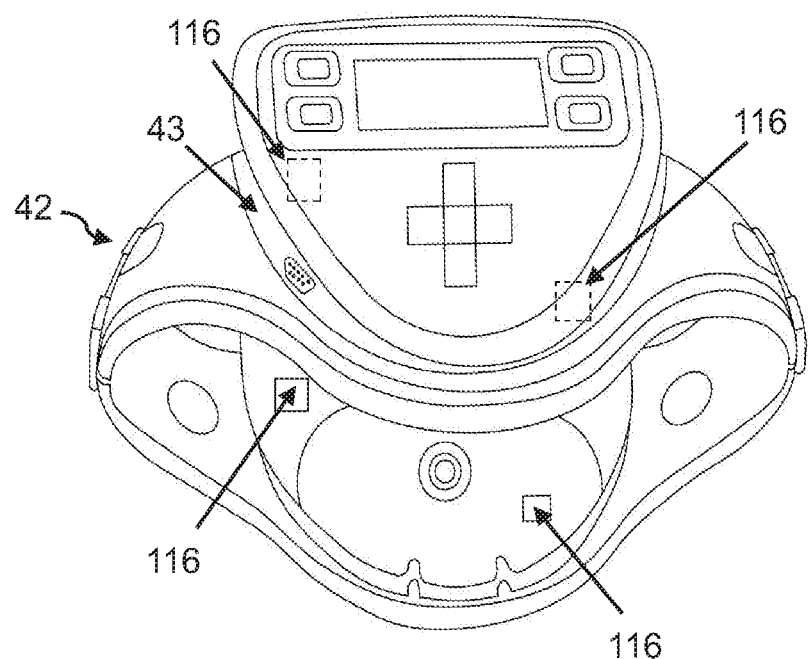
FIG. 9C is a perspective view of the embodiment illustrated in FIG. 9A.

FIGS. 9A-9C illustrate another embodiment of the present invention, for use with a DPI inhaler 38.

The DPI inhaler 38 is in the form of a disk which includes a store of dry powder (not shown) for the treatment of a respiratory disease such as asthma. The inhaler 38 includes a powder release lever 39 and a mouthpiece 40. As a skilled addressee would understand a portion 38a of the DPI inhaler 38 must be rotated from a closed position to an open position to reveal and provide access to the powder release lever 39 and the mouthpiece 40 by the user. In normal use, the lever 39 is moved in the direction indicated by arrow 41, and this releases a metered dose of dry powder into an internal cavity (not shown) adjacent the mouthpiece 40. The patient may then inhale the powder by sucking strongly through the mouthpiece 40.

Releasably attached to the inhaler 38 is a device, generally indicated by arrow 42, for monitoring patient usage of the inhaler 38. FIG. 9B shows the DPI inhaler in the closed position, where the mouthpiece and the lever are not accessible. To reveal the mouthpiece 40 and the lever 39, as shown in FIG. 9A, the patient moves the portion 38a of the inhaler 38 in direction indicated by arrow 141, shown in FIG. 9B.

The device 42 includes a housing 43 which is substantially U-shaped and which is designed to slide over and fit snugly around a substantial portion of the inhaler 38. The housing 43 is also provided with a hinge 46 to enable the housing 43 to hingedly open up into two halves in order to be fitted to the inhaler 38, if so desired or required.

As shown in FIGS. 9A and 9B, inhaler portion 38a is shown to indicate which part of the inhaler 38 moves relative to the inhaler mouthpiece cover to reveal the mouthpiece 40 and the lever 39. Portion 38a points to the element of the inhaler 38. Arrow 141 shows in which direction the inhaler portion 38a needs to be moved relative to the mouthpiece cover of the inhaler. FIGS. 9A-9C also show possible locations 116 of the optical dose counter on the inner surface of the device 42.

The housing 43 includes an optical dose counter (not shown) which is able to determine when a dose of medicament has been dispensed from the inhaler 38 by transmitting optical signals through the inhaler 38, and sensing movement of the internal parts of the inhaler 38 during the dispensing of a dose of powder. The optical dose counter 116 includes a light transmitter(s) (not shown) and a light receiver(s) (not shown), both housed within the housing 43. In one embodiment, the light receiver(s) may be positioned substantially opposite the light transmitter(s) in order to receive a substantially direct beam of light. In such an embodiment, the movement of part(s) within the inhaler during the dispensing of a dose may temporarily block the beam of light, thus enabling the dose counter to register that a dose of medicament has been dispensed.

In an alternative embodiment, the light transmitter(s) may transmit a normal beam of light, which will generally disperse outwardly from the point of transmission. The movement of part(s) within the inhaler during the dispensing of a dose will therefore affect the light signal, for example by the light reflecting off the part(s) as they move. This will alter the intensity of light being received by the light receiver(s), thus enabling the dose counter to register that a dose of medicament has been dispensed. In such an embodiment, it is not necessary that the moving part(s) actually block the light signal to enable a dose to be detected and/or counted. Hence, the light transmitter(s) and light receiver(s) need not necessarily be positioned substantially opposite each other. It is also possible that the light transmitter(s) and light receiver(s) could be positioned next to each other or side by side.

Having regard to FIG. 9C, alternative positions of the optical dose counter 116 are illustrated. In some embodiments, the light transmitter(s) and the light receiver(s) will be positioned substantially opposite each other. In other embodiments, the light transmitter(s) and the light receiver(s) may be positioned next to each other. The device 42 also includes an electronic control module (not shown in FIG. 9A-9C, but also represented in the system block diagram of FIG. 10) which works substantially the same as the electronic control module associated with the pMDI inhaler 2. Furthermore, the housing 43 includes a user interface which includes an LCD screen 44 and operational buttons 45.

The device 42 only differs from the device 1 in its shape and design—in order for the device 42 to be able to fit a DPI inhaler 38 as compared to a pMDI inhaler 2. The device 42 may therefore have some or all of the same features and operational capabilities as the device 1 described previously in relation to the pMDI inhaler 2. For convenience therefore, a detailed description of the workings of the device 42 is not considered necessary, and the reader is instead referred to the detailed description previously provided in relation to the workings of the device 1 for use with the pMDI inhaler 2.

An advantage associated with the device (1, 42) generally is that it may serve as both a patient compliance monitor (for example to monitor patient compliance in relation to a medicament such as a preventer or combination medicament) and also as a device to monitor patient usage of an emergency drug such as a reliever. The patient (or a third party such as a parent or medical practitioner) may therefore obtain important and useful information relating to a patient's compliance generally, as well as the ability to be forewarned of the possibility of an event such as an exacerbation event.

The invention may be particularly useful for use with large clinical trials, for example those used to determine whether a particular medicament may have unwanted side effects. Such trials may include a number of people in a trial group (those using the medicament being tested) and a number of people in the control group (those not using the medicament being tested). There may be upwards of 3000 people in each group, and the results of the clinical trial may be very important. Hence, it is imperative that the people running the trial know for certain whether the trial group and/or control group has been taking the medicament as prescribed, and over the set time period of the trial (which may be many months). Because the present invention is reusable in relation to each new container of medicament being tested, it may be used by each patient in the trial, for the entire duration of the trial.

The invention may also be useful as a diagnostic tool by a respiratory specialist for use with their patients. For example, a specialist may be unsure whether a patient has asthma or heart disease. The specialist may therefore supply the device to a patient for use with asthma medicament over a period of time and the usage information being used by the specialist to diagnose the disease. Moreover, the patient may return the device to the specialist at the conclusion of the trial, whereby it may be supplied the next patient of the specialist.

The invention may also be useful as a self-diagnosis device for a patient. That is, a patient may use the device to self-monitor their own personal usage and make conclusions or changes as a result. Alternatively, it may be used by a parent or care giver as a tool for ascertaining if someone in their care has been taking their medicament correctly, or otherwise.

This may be of particular advantage during clinical trials where the ongoing monitoring of a patient is being undertaken over a considerable time period, and perhaps whereby the patient changes medication half way through the trial.

While the embodiments described above are currently preferred, it will be appreciated that a wide range of other variations might also be made within the general spirit and scope of the invention and/or as defined by the appended claims.

What is claimed is:

1. A device for monitoring usage of a disk-shaped, dry powder medicament inhaler that has a structure sufficient in itself to deliver doses of medicament, the medicament inhaler including: a medicament container configured for housing medicament, where said medicament container defines a mouthpiece; an exterior surface; and a lever that is configured for movement to thereby enable delivery of each dose of medicament into the mouthpiece so as to be user accessible via an airflow path, the device comprising:
   a housing that:
      includes first and second sides that are connected by a hinge and configured to move between an open position to enable insertion of the medicament inhaler and a closed position to retain the medicament inhaler,
      is at least in part U-shaped in cross-section, and
      defines an outer surface, and is configured to receive at least a portion of the medicament inhaler therein,
      the housing being configured to be releasably attachable to the exterior surface of the medicament inhaler so as to enable repeated attachment to and removal from the medicament inhaler,
   the housing defining a retaining portion that is configured to engage with at least a portion of the exterior surface of the of the medicament inhaler so as to retain the medicament inhaler in the housing,
   wherein the at least a portion of the exterior surface of the medicament inhaler includes a mouthpiece opening that defines the mouthpiece, and the housing, in the closed position, includes a housing opening that is configured to surround at least a portion of the mouthpiece opening so as to allow a user to access the mouthpiece, so as to suck on the mouthpiece and inhale the medicament;
   a sensor that is supported by the housing and configured to determine if a dose of medicament has been dispensed from the medicament inhaler, the sensor being configured to identify dispensation of the medicament without requiring any structural alterations to the medicament inhaler, the sensor including at least one electromagnetic signal transmitter located on one of the first side or the second side of the housing and configured to transmit an electromagnetic signal through the exterior surface of the medicament inhaler and through the medicament inhaler, and at least one electromagnetic signal receiver located on the other of the first side or the second side of the housing and configured to receive the electromagnetic signal after it is transmitted through the exterior surface of the medicament inhaler and through the medicament inhaler; and
   the housing including a user interface that is integrated into and supported by the housing, and the user interface configured to enable user interaction with the device;
   wherein the housing and sensor are disposed outside of the medicament inhaler airflow path to avoid impeding airflow characteristics within the medicament inhaler.

2. The device of claim 1, wherein the housing is translucent or transparent.

3. The device of claim 1, the user interface including a screen and operational buttons that are in communication with a controller, and the housing includes the controller.

4. The device of claim 1, the housing opening configured to surround and provide access to the lever.

5. The device of claim 4, the movement of the lever being along a portion of the housing opening.

6. The device of claim 5, wherein the movement of the lever is configured to release a metered dose of dry powder into an internal cavity of the medicament container, and the internal cavity being adjacent to the mouthpiece.

7. The device of claim 1, wherein the movement of the lever is configured to release a metered dose of dry powder into an internal cavity of the medicament container, and the internal cavity being adjacent to the mouthpiece.

8. The device of claim 7, the housing including a controller and the user interface, the user interface including a screen and operational buttons that are in communication with the controller, and
   the controller configured to monitor doses from the medicament container.

9. The device of claim 8, the sensor including an optical dose counter, and
   the controller is configured to monitor the doses from the medicament container using the optical dose counter.

10. A method for fitting the device for monitoring usage of claim 1 to a disk-shaped, dry powder medicament inhaler that has a structure sufficient in itself to deliver doses of medicament, the medicament inhaler including: a medicament container configured for housing medicament, where said medicament container defines a delivery aperture; an exterior surface; and a lever that is configured for movement to thereby enable delivery of each dose of medicament into the delivery aperture so as to be user accessible via an airflow path, the method including the steps of:

handling the housing of the device for monitoring usage of claim 1;

moving the first and second sides of the housing connected by the hinge to an open position to enable insertion of the medicament inhaler, placing the medicament inhaler on the first or the second side of the housing, such that:

the retaining portion of the housing engages with at least a portion of the exterior surface of the medicament inhaler, so as to retain the medicament inhaler in the housing;

the housing is disposed outside the medicament inhaler airflow path to avoid impeding airflow characteristics within the medicament inhaler;

the housing is disposed outside the range of movement of the lever configured to delivery dose of medicament; and moving the first and second sides of the housing connected by the hinge to a closed position to retain the medicament inhaler in the housing.

\* \* \* \* \*